(12) United States Patent
Braun et al.

(10) Patent No.: US 7,975,344 B2
(45) Date of Patent: Jul. 12, 2011

(54) TOOTHBRUSH HEAD

(75) Inventors: Phillip M. Braun, Exeter, RI (US);
Alexander T. Chenvainu, Sudbury, MA (US)

(73) Assignee: The Gillette Company, Boston, MA (US)

(*) Notice: Subject to any disclaimer, the term of this patent is extended or adjusted under 35 U.S.C. 154(b) by 36 days.

(21) Appl. No.: 11/825,387

(22) Filed: Jul. 6, 2007

(65) Prior Publication Data
US 2007/0251040 A1 Nov. 1, 2007

Related U.S. Application Data

(63) Continuation of application No. 11/799,733, filed on May 2, 2007, now abandoned, which is a continuation of application No. 10/389,448, filed on Mar. 14, 2003, now abandoned.

(51) Int. Cl.
*A46B 9/04* (2006.01)
(52) U.S. Cl. .............. 15/110; 15/167.1; 15/194; 15/201
(58) Field of Classification Search ............ 15/110–111, 15/167.1, 185–188, 201–203, 194; 601/141
See application file for complete search history.

(56) References Cited

U.S. PATENT DOCUMENTS

| | | |
|---|---|---|
| 301,644 A | 7/1884 | Thompson |
| 429,839 A | 6/1890 | Beissbarth |
| 601,405 A | 3/1898 | Shepherd |
| 819,444 A | 5/1906 | Monroe |
| 1,022,920 A | 4/1912 | Anderson |
| 1,063,523 A | 6/1913 | Farrar |
| 1,128,139 A * | 2/1915 | Hoffman .......... 15/117 |
| 1,142,698 A | 6/1915 | Grove et al. |
| 1,172,109 A * | 2/1916 | Cammack .......... 15/172 |
| 1,191,556 A | 7/1916 | Blake |
| 1,268,544 A | 12/1916 | Cates |
| 1,251,250 A | 12/1917 | Libby |
| 1,323,042 A | 11/1919 | Gardner |
| 1,526,267 A | 9/1924 | Dessau |
| 1,673,638 A | 6/1928 | Peterson |
| 1,693,229 A | 11/1928 | Felmar |
| 1,698,128 A | 1/1929 | Funk |
| 1,704,564 A | 3/1929 | Friedland |
| 1,753,290 A | 4/1930 | Graves |
| 1,758,632 A | 5/1930 | Wagner |

(Continued)

FOREIGN PATENT DOCUMENTS

AU 44639693 8/1993

(Continued)

OTHER PUBLICATIONS

Office Action for U.S. Appl. No. 10/389,448; P&G Case Z-3801; dated Jun. 2, 2006.

(Continued)

*Primary Examiner* — Laura C Guidotti
(74) *Attorney, Agent, or Firm* — George H. Leal; James C. Vago

(57) ABSTRACT

A toothbrush has a handle and a head part, on which bristle filaments and at least one flexible cleaning element are arranged. The at least one flexible cleaning element is arranged on a carrier element which consists of a hard material and is connected to the head part. A process for producing such a toothbrush is also disclosed.

28 Claims, 10 Drawing Sheets

U.S. PATENT DOCUMENTS

| | | | |
|---|---|---|---|
| 1,764,130 A | 6/1930 | Vardeman | |
| 1,796,893 A | 3/1931 | McVeigh | |
| 1,797,946 A | 3/1931 | Eichel | |
| 1,863,389 A | 5/1931 | Anderson | |
| 1,840,246 A | 1/1932 | Newman | |
| 1,908,510 A | 5/1933 | Dodson | |
| 1,924,152 A * | 8/1933 | Coney et al. | 15/167.1 |
| 1,963,389 A | 6/1934 | Vardeman | |
| 1,993,662 A | 3/1935 | Green | |
| 2,042,239 A * | 5/1936 | Planding | 15/110 |
| 2,155,473 A | 9/1936 | Coleman | |
| 2,088,839 A | 8/1937 | Coney et al. | |
| 2,117,174 A | 5/1938 | Jones | |
| 2,129,082 A | 9/1938 | Byrer | |
| 2,139,245 A | 12/1938 | Ogden | |
| 2,154,846 A | 4/1939 | Heymann et al. | |
| 2,164,219 A | 6/1939 | McGerry | |
| 2,172,624 A | 9/1939 | Gabriel et al. | |
| 2,176,309 A | 10/1939 | Love et al. | |
| 2,189,175 A | 2/1940 | Jackson | |
| 2,206,726 A | 7/1940 | Lasater | |
| 2,219,753 A | 10/1940 | Seguin | |
| 2,225,331 A | 12/1940 | Campbell | |
| 2,238,603 A | 4/1941 | Runnels | |
| 2,244,699 A | 6/1941 | Hosey | |
| 2,246,867 A | 6/1941 | Thomas et al. | |
| 2,263,802 A | 11/1941 | Grusin | |
| 2,266,195 A | 12/1941 | Lay | |
| 2,279,355 A | 4/1942 | Wilensky | |
| 2,312,828 A | 3/1943 | Adamsson | |
| 2,326,632 A | 8/1943 | Friedman | |
| 2,328,998 A | 9/1943 | Radford | |
| 2,364,205 A | 12/1944 | Fuller | |
| 2,486,203 A * | 10/1949 | Pieper | 15/203 |
| 2,486,847 A | 11/1949 | Hokett | |
| 2,556,691 A | 6/1951 | Harshbarger | |
| 2,604,649 A | 7/1952 | Stephenson et al. | |
| 2,637,870 A * | 5/1953 | Cohen | 15/188 |
| 2,702,914 A | 3/1955 | Kittle et al. | |
| 2,832,088 A | 4/1958 | Peilet et al. | |
| 2,882,544 A | 4/1959 | Hadidian | |
| 2,935,755 A | 5/1960 | Leira et al. | |
| 3,007,441 A | 11/1961 | Eyer | |
| 3,016,554 A | 1/1962 | Peterson | |
| 3,050,072 A | 8/1962 | Diener | |
| 3,103,027 A | 9/1963 | Birch | |
| 3,110,918 A | 11/1963 | Tate, Jr. | |
| 3,128,487 A | 4/1964 | Vallis | |
| 3,129,449 A | 4/1964 | Cyzer | |
| 3,159,859 A | 12/1964 | Rasmussen | |
| 3,177,509 A | 4/1965 | Cyzer | |
| 3,230,562 A | 1/1966 | Birch | |
| 3,258,805 A | 7/1966 | Rossnan | |
| 3,295,156 A | 1/1967 | Brant | |
| 3,302,230 A | 2/1967 | Poppelman | |
| 3,316,576 A | 5/1967 | Urbrush | |
| 3,327,339 A | 6/1967 | Lemelson | |
| 3,359,588 A | 12/1967 | Kobler | |
| 3,398,421 A | 8/1968 | Rashbaum | |
| 3,403,070 A | 9/1968 | Lewis, Jr. | |
| 3,411,979 A | 11/1968 | Lewis | |
| RE26,688 E | 10/1969 | Lemelson | |
| 3,553,759 A | 1/1971 | Kramer et al. | |
| 3,613,143 A | 10/1971 | Muhler et al. | |
| 4,033,008 A | 7/1977 | Warren et al. | |
| 4,081,877 A | 4/1978 | Vitale | |
| 4,114,222 A | 9/1978 | Serediuk | |
| 4,128,910 A | 12/1978 | Nakata et al. | |
| 4,156,620 A | 5/1979 | Clemens | |
| 4,202,361 A | 5/1980 | Bills | |
| 4,263,691 A | 4/1981 | Pakarnseree | |
| 4,277,862 A | 7/1981 | Weideman | |
| 4,288,883 A | 9/1981 | Dolinsky | |
| 4,356,585 A | 11/1982 | Protell et al. | |
| 4,373,541 A | 2/1983 | Nishioka | |
| 4,391,951 A | 7/1983 | Scheetz | |
| 4,403,623 A | 9/1983 | Mark | |
| 4,409,701 A | 10/1983 | Perches | |
| 4,429,434 A | 2/1984 | Sung-Shan | |
| 4,472,853 A | 9/1984 | Rauch | |
| 4,476,280 A | 10/1984 | Poppe et al. | |
| 4,480,351 A | 11/1984 | Koffler | |
| 4,517,701 A | 5/1985 | Sanford, Jr. | |
| 4,525,531 A | 6/1985 | Zukosky et al. | |
| 4,534,081 A | 8/1985 | Spademan | |
| 4,545,087 A | 10/1985 | Nahum | |
| 4,585,416 A | 4/1986 | DeNiro et al. | |
| 4,603,166 A | 7/1986 | Poppe et al. | |
| 4,616,064 A | 10/1986 | Zukosky et al. | |
| 4,617,342 A | 10/1986 | Poppe et al. | |
| 4,617,694 A | 10/1986 | Bori | |
| 4,623,495 A | 11/1986 | Degoix et al. | |
| 4,633,542 A | 1/1987 | Taravel | |
| 4,654,922 A | 4/1987 | Chen | |
| 4,672,706 A | 6/1987 | Hill | |
| 4,691,405 A | 9/1987 | Reed | |
| 4,694,844 A | 9/1987 | Berl et al. | |
| 4,706,322 A | 11/1987 | Nicolas | |
| 4,751,761 A | 6/1988 | Breitschmid | |
| 4,776,054 A | 10/1988 | Rauch | |
| 4,783,874 A | 11/1988 | Perches et al. | |
| 4,802,255 A | 2/1989 | Breuer et al. | |
| 4,833,194 A | 5/1989 | Kuan et al. | |
| 4,845,795 A | 7/1989 | Crawford et al. | |
| 4,852,202 A | 8/1989 | Ledwitz | |
| 4,882,803 A | 11/1989 | Rogers et al. | |
| 4,892,698 A | 1/1990 | Weihrauch | |
| 4,894,880 A | 1/1990 | Aznavoorian | |
| 4,913,133 A | 4/1990 | Tichy | |
| 4,979,782 A | 12/1990 | Weihrauch | |
| 4,989,287 A | 2/1991 | Scherer | |
| 4,991,249 A | 2/1991 | Suroff | |
| 5,020,179 A | 6/1991 | Scherer | |
| 5,021,475 A | 6/1991 | Isayev | |
| 5,034,450 A | 7/1991 | Betz et al. | |
| 5,040,260 A | 8/1991 | Michaels | |
| D325,821 S | 5/1992 | Schwartz | |
| 5,114,214 A | 5/1992 | Barman | |
| 5,120,225 A | 6/1992 | Amit | |
| 5,137,039 A | 8/1992 | Klinkhammer | |
| 5,142,724 A | 9/1992 | Park | |
| 5,165,131 A | 11/1992 | Staar | |
| 5,184,368 A | 2/1993 | Holland | |
| 5,186,627 A | 2/1993 | Amit et al. | |
| 5,228,166 A | 7/1993 | Gomez | |
| 5,269,038 A | 12/1993 | Bradley | |
| D345,054 S | 3/1994 | Spence, Jr. | |
| 5,291,878 A | 3/1994 | Lombardo et al. | |
| 5,313,909 A | 5/1994 | Tseng et al. | |
| 5,318,352 A | 6/1994 | Holland | |
| 5,321,726 A | 6/1994 | Kafadar | |
| 5,325,560 A | 7/1994 | Pavone et al. | |
| 5,334,646 A | 8/1994 | Chen | |
| D350,851 S | 9/1994 | Spence, Jr. | |
| 5,350,248 A | 9/1994 | Chen | |
| 5,357,644 A | 10/1994 | Theriault | |
| 5,392,483 A | 2/1995 | Heinzelman et al. | |
| 5,398,366 A * | 3/1995 | Bradley | 15/167.1 |
| 5,407,254 A | 4/1995 | Hegemann | |
| 5,421,726 A | 6/1995 | Okada | |
| 5,435,032 A | 7/1995 | McDougall | |
| 5,458,400 A | 10/1995 | Meyer | |
| 5,476,384 A | 12/1995 | Giuliani et al. | |
| 5,524,319 A | 6/1996 | Avidor | |
| 5,528,786 A | 6/1996 | Porat et al. | |
| 5,535,474 A | 7/1996 | Salazar | |
| 5,546,626 A | 8/1996 | Chung | |
| 5,590,434 A | 1/1997 | Imai | |
| 5,593,213 A | 1/1997 | Meessmann | |
| 5,604,951 A | 2/1997 | Shipp | |
| 5,628,082 A | 5/1997 | Moskovich | |
| 5,651,157 A | 7/1997 | Hahn | |
| 5,678,275 A | 10/1997 | Derfner | |
| D386,617 S | 11/1997 | Shyu | |
| 5,706,542 A | 1/1998 | Okaka | |
| 5,722,106 A | 3/1998 | Masterman et al. | |
| 5,723,543 A | 3/1998 | Modic | |

| | | |
|---|---|---|
| 5,735,011 A | 4/1998 | Asher |
| 5,778,474 A | 7/1998 | Shek |
| 5,791,007 A | 8/1998 | Tsai |
| 5,799,354 A | 9/1998 | Amir |
| 5,802,656 A | 9/1998 | Dawson et al. |
| 5,813,079 A | 9/1998 | Halm |
| 5,823,633 A | 10/1998 | Weihrauch |
| D401,414 S | 11/1998 | Vrignaud |
| 5,836,033 A | 11/1998 | Berge |
| 5,839,148 A | 11/1998 | Volpenhein |
| 5,842,249 A | 12/1998 | Sato |
| 5,864,915 A | 2/1999 | Ra |
| 5,896,614 A | 4/1999 | Flewitt |
| 5,930,860 A | 8/1999 | Shipp |
| 5,946,759 A | 9/1999 | Cann |
| 5,970,564 A | 10/1999 | Inns et al. |
| 5,974,619 A * | 11/1999 | Weihrauch ............. 15/186 |
| 5,987,681 A | 11/1999 | Hahn et al. |
| 5,987,688 A * | 11/1999 | Roberts et al. ............. 15/167.1 |
| 5,991,959 A | 11/1999 | Raven et al. |
| 6,018,840 A | 2/2000 | Guay et al. |
| 6,035,476 A | 3/2000 | Underwood et al. |
| 6,058,541 A | 5/2000 | Masterman et al. |
| 6,067,684 A | 5/2000 | Kweon |
| 6,088,870 A | 7/2000 | Hohlbein |
| 6,112,361 A | 9/2000 | Brice |
| 6,138,310 A | 10/2000 | Porper et al. |
| 6,151,745 A | 11/2000 | Roberts et al. |
| 6,161,245 A | 12/2000 | Weihrauch |
| 6,178,582 B1 | 1/2001 | Halm |
| 6,199,242 B1 | 3/2001 | Masterman et al. |
| 6,202,241 B1 | 3/2001 | Hassell et al. |
| D440,048 S | 4/2001 | Beals et al. |
| 6,209,164 B1 | 4/2001 | Sato |
| D443,985 S | 6/2001 | Beals et al. |
| 6,253,404 B1 | 7/2001 | Boland et al. |
| 6,286,173 B1 | 9/2001 | Briones |
| 6,290,302 B1 | 9/2001 | Boucherie |
| 6,290,303 B1 | 9/2001 | Boucherie |
| 6,298,516 B1 | 10/2001 | Beals et al. |
| 6,308,367 B1 | 10/2001 | Beals et al. |
| 6,363,565 B1 | 4/2002 | Paffrath |
| 6,389,634 B1 * | 5/2002 | Devlin et al. ............. 15/110 |
| 6,391,445 B1 * | 5/2002 | Weihrauch ............. 428/373 |
| 6,405,401 B1 | 6/2002 | Hellerud et al. |
| 6,421,865 B1 | 7/2002 | McDougall |
| 6,421,867 B1 | 7/2002 | Weihrauch |
| 6,453,497 B1 | 9/2002 | Chiang et al. |
| 6,463,618 B1 | 10/2002 | Zimmer |
| 6,477,729 B1 | 11/2002 | Ben-Ari |
| 6,513,182 B1 | 2/2003 | Calebrese et al. |
| 6,553,604 B1 * | 4/2003 | Braun et al. ............. 15/167.1 |
| 6,564,416 B1 | 5/2003 | Claire et al. |
| 6,571,417 B1 | 6/2003 | Gavney, Jr. et al. |
| 6,658,688 B2 | 12/2003 | Gavney, Jr. |
| 6,701,565 B2 | 3/2004 | Hafemann |
| 6,725,490 B2 | 4/2004 | Blaustein et al. |
| 6,776,597 B2 | 8/2004 | Buhler |
| 6,807,703 B2 | 10/2004 | Van Gelder et al. |
| 6,820,300 B2 | 11/2004 | Gavney, Jr. |
| 6,826,797 B1 | 12/2004 | Chenvainu et al. |
| 6,859,969 B2 | 3/2005 | Gavney, Jr. et al. |
| 6,889,401 B2 | 5/2005 | Fattori et al. |
| 6,892,412 B2 | 5/2005 | Gatzmeyer et al. |
| 6,892,413 B2 | 5/2005 | Blaustein et al. |
| 6,918,154 B2 | 7/2005 | Ben-Ari |
| 6,931,688 B2 | 8/2005 | Moskovich et al. |
| 6,938,294 B2 | 9/2005 | Fattor et al. |
| 6,983,507 B2 | 1/2006 | McDougall |
| 6,988,777 B2 | 1/2006 | Pfenniger et al. |
| 6,993,804 B1 * | 2/2006 | Braun et al. ............. 15/110 |
| 7,008,225 B2 | 3/2006 | Ito et al. |
| 7,160,508 B2 | 1/2007 | Lee |
| 7,222,381 B2 | 5/2007 | Kraemer |
| 7,225,494 B2 | 6/2007 | Chan |
| 7,251,849 B2 | 8/2007 | Moskovich |
| 7,392,562 B2 | 7/2008 | Boland et al. |
| 2001/0007161 A1 | 7/2001 | Masterman et al. |
| 2001/0013151 A1 * | 8/2001 | Gelder et al. ............. 15/167.1 |
| 2001/0020314 A1 | 9/2001 | Calabrese |
| 2002/0004964 A1 * | 1/2002 | Luchino et al. ............. 15/167.1 |
| 2002/0084550 A1 | 7/2002 | Roberts et al. |
| 2002/0192621 A1 | 12/2002 | Ben-Air |
| 2003/0033680 A1 | 2/2003 | Davies et al. |
| 2003/0033682 A1 | 2/2003 | Davies et al. |
| 2003/0041402 A1 | 3/2003 | Stein et al. |
| 2003/0066147 A1 | 4/2003 | Roh |
| 2003/0077107 A1 | 4/2003 | Kuo |
| 2003/0079304 A1 | 5/2003 | Dworzan |
| 2003/0084525 A1 | 5/2003 | Blaustein et al. |
| 2003/0140440 A1 | 7/2003 | Gavney, Jr. |
| 2003/0159224 A1 | 8/2003 | Fischer et al. |
| 2003/0196283 A1 | 10/2003 | Eliav et al. |
| 2003/0229959 A1 | 12/2003 | Gavney, Jr. et al. |
| 2004/0010869 A1 | 1/2004 | Fattori et al. |
| 2004/0025275 A1 | 2/2004 | Moskovich et al. |
| 2004/0060132 A1 | 4/2004 | Gatzemeyer et al. |
| 2004/0060133 A1 | 4/2004 | Eliav |
| 2004/0060137 A1 | 4/2004 | Eliav |
| 2004/0068809 A1 | 4/2004 | Weng |
| 2004/0083566 A1 | 5/2004 | Blaustein et al. |
| 2004/0084063 A1 | 5/2004 | Vago et al. |
| 2004/0123409 A1 | 7/2004 | Dickie |
| 2004/0128784 A1 | 7/2004 | Ben-Ari |
| 2004/0168271 A1 | 9/2004 | McDougall |
| 2004/0177458 A1 | 9/2004 | Chan et al. |
| 2004/0177462 A1 | 9/2004 | Duff et al. |
| 2004/0221409 A1 | 11/2004 | Gavney, Jr. |
| 2004/0231076 A1 | 11/2004 | Gavney, Jr. |
| 2004/0231082 A1 | 11/2004 | Gavney, Jr. |
| 2004/0237236 A1 | 12/2004 | Gavney, Jr. |
| 2004/0261203 A1 | 12/2004 | Dworzan |
| 2005/0015901 A1 | 1/2005 | Gavney, Jr. |
| 2005/0060822 A1 | 3/2005 | Chenvainu et al. |
| 2005/0235439 A1 | 10/2005 | Braun et al. |
| 2005/0273961 A1 | 12/2005 | Moskovich et al. |
| 2006/0272112 A9 | 12/2006 | Braun et al. |
| 2008/0060155 A1 | 3/2008 | Braun et al. |
| 2009/0172900 A1 | 7/2009 | Brown, Jr. et al. |
| 2010/0162499 A1 | 7/2010 | Braun et al. |

FOREIGN PATENT DOCUMENTS

| | | |
|---|---|---|
| CA | 454913 | 3/1949 |
| CA | 2483825 | 10/2004 |
| CH | 103 194 | 1/1924 |
| CH | 169312 | 5/1934 |
| CH | 609238 | 2/1979 |
| CN | 2119280 U | 10/1992 |
| DE | 558 852 | 9/1932 |
| DE | 813 990 | 7/1949 |
| DE | 1 883 020 | 11/1963 |
| DE | 1210409 | 2/1966 |
| DE | 7343826 U | 11/1974 |
| DE | 2 402 785 | 7/1975 |
| DE | DT 25 00132 A1 | 7/1976 |
| DE | DT 25 46 712 A1 | 4/1977 |
| DE | 2715414 A1 | 10/1978 |
| DE | 82 15 266.7 U1 | 9/1982 |
| DE | 35 29 953 A1 | 3/1987 |
| DE | 37 44 630 A1 | 7/1989 |
| DE | 3928919 | 3/1991 |
| DE | 42 07 968 | 9/1993 |
| DE | 94 00 231.2 U1 | 3/1994 |
| DE | 4412301 | 10/1995 |
| DE | 19817704 | 10/1999 |
| DE | 29919053 | 12/2000 |
| DE | 100 28 530 A1 | 12/2001 |
| DK | 0076598 | 11/1953 |
| EP | DE 75 33 143 U | 2/1976 |
| EP | 0 189 816 A2 | 8/1986 |
| EP | 0322562 | 7/1989 |
| EP | 0 360 766 A1 | 3/1990 |
| EP | 0 704 179 A1 | 4/1996 |
| EP | 0 783 850 B1 | 3/2001 |
| EP | 1 080 664 | 3/2001 |
| EP | 0 870 440 B1 | 12/2001 |
| EP | 1 449 496 B1 | 9/2008 |
| FR | 459 442 | 11/1913 |

| | | |
|---|---|---|
| FR | 936529 | 6/1948 |
| FR | 1075171 | 10/1954 |
| FR | 2541100 | 8/1984 |
| FR | 2548528 | 1/1985 |
| FR | 2559361 | 8/1985 |
| FR | 2 612 751 | 9/1988 |
| FR | 2 616 306 | 12/1988 |
| FR | JP 08257043 | 8/1996 |
| FR | 2789887 | 2/1999 |
| FR | 2 789 887 | 8/2000 |
| GB | 193 601 A | 3/1923 |
| GB | 280 067 A | 11/1927 |
| GB | 378 129 A | 8/1932 |
| GB | 490 892 A | 8/1938 |
| GB | 690 422 A | 4/1953 |
| GB | 1 164 597 A | 9/1969 |
| GB | 1 325 860 A | 8/1973 |
| GB | 1 537 526 | 12/1978 |
| GB | 2137080 | 10/1984 |
| GB | 2 214 420 A | 9/1989 |
| GB | 2247297 | 2/1992 |
| GB | 2 354 432 A | 3/2001 |
| JP | 50-11769 | 2/1975 |
| JP | 51-056165 U | 5/1976 |
| JP | 52-125962 U | 9/1977 |
| JP | 58-091931 U | 6/1983 |
| JP | 61-187531 U | 11/1986 |
| JP | 63-066928 U | 5/1988 |
| JP | 1-72128 | 5/1989 |
| JP | 2-119031 | 7/1990 |
| JP | 2-180203 | 7/1990 |
| JP | 3-3226 | 1/1991 |
| JP | 3-312978 | 9/1991 |
| JP | 4-128627 | 11/1992 |
| JP | 5-69342 | 3/1993 |
| JP | 05-76416 | 3/1993 |
| JP | 05096597 | 4/1993 |
| JP | 5-123222 | 5/1993 |
| JP | 6-327517 A2 | 11/1994 |
| JP | 08103326 | 4/1996 |
| JP | 08103332 | 4/1996 |
| JP | 61-90877 | 5/1996 |
| JP | 08299372 | 11/1996 |
| JP | 9-140456 | 3/1997 |
| JP | 9-187319 A2 | 7/1997 |
| JP | 2000-157338 | 6/2000 |
| JP | 2000-300345 | 10/2000 |
| JP | 2000-300347 | 10/2000 |
| JP | 2000-308524 | 11/2000 |
| JP | 2001-190333 | 7/2001 |
| JP | 2001-507360 | 7/2001 |
| JP | 2002-010832 | 1/2002 |
| JP | 2002-248118 | 9/2002 |
| JP | 200361986 | 3/2003 |
| JP | 2003093415 | 4/2003 |
| JP | 2003164473 | 6/2003 |
| RU | 2045216 | 10/1995 |
| SU | 1687243 | 10/1991 |
| SU | 1752336 | 8/1992 |
| WO | WO 91/05088 | 4/1991 |
| WO | WO 92/04589 | 3/1992 |
| WO | WO 9324034 | 12/1993 |
| WO | WO 95/01113 A1 | 1/1995 |
| WO | WO 96/15696 | 5/1996 |
| WO | WO 97/14330 | 4/1997 |
| WO | WO 98/01055 | 1/1998 |
| WO | WO 98/18364 | 5/1998 |
| WO | WO 9937181 | 7/1999 |
| WO | WO 00/21406 | 4/2000 |
| WO | WO 00/30495 | 6/2000 |
| WO | WO 00/34022 | 6/2000 |
| WO | WO 00/47083 | 8/2000 |
| WO | WO 00/64307 | 11/2000 |
| WO | WO 00/76369 A2 | 12/2000 |
| WO | WO 01/06947 A1 | 1/2001 |
| WO | WO 01/06946 A1 | 2/2001 |
| WO | WO 01/21036 A1 | 3/2001 |
| WO | WO 01/43586 | 6/2001 |
| WO | WO 01/87101 A2 | 11/2001 |
| WO | WO 01/89344 | 11/2001 |
| WO | WO 02/05679 A1 | 1/2002 |
| WO | WO 02/11583 * | 2/2002 |
| WO | WO 02/19942 A1 | 3/2002 |
| WO | WO 02/38004 | 5/2002 |
| WO | WO 02/45617 | 6/2002 |
| WO | WO 03/086140 A1 | 10/2003 |
| WO | WO 2004/014181 A1 | 2/2004 |

OTHER PUBLICATIONS

Office Action for U.S. Appl. No. 10/389,448; P&G Case Z-3801; dated Oct. 26, 2007.
Office Action for U.S. Appl. No. 10/389,448; P&G Case Z-3801; dated Jul. 2, 2008.
Office Action for U.S. Appl. No. 10/820,562; P&G Case Z-3710E; dated Dec. 2, 2008.
Board Opinion from the Chinese Patent Office with regard to Application No. 01806615.1 dated Jul. 17, 2007 with translation.
"Santroprene Rubber Physical Properties Guide, Tensile Properties, Dynamic Mechanical Properties, Tension and Compression Set, Fatigue Resistance", Advanced Elastomer Systems, pp. 2-19, Undated.
"Distinctive Plastics—Multi-Component Molding" http://www.distinctiveplastics.com/html/?id=2 copyright 2006.
"Plastics-Determination of flexural properties", British Standard, BS EN ISO 178:2003, Apr. 9, 2003.
Plastics Extrusion Technology Handbook Chapter Seven, Coextrusion and Dual-Extrusion Technology, pp. 168-189.
Modern Plastic Encyclopedia, 67:168-175, 1990.
Pebax 3533 SA 00, "Base Polymer for Structural Hot Melt Adhesives".
Product Literature, Kraton Polymers, pp. 13-21.
"Standard Test Methods for Flexural Properties of Unreinforced and Reinforced Plastics and Electrical Insulating Materials [Metric]", American Society for Testing Materials, Designation: D790M-93 Metric, pp. 1-9, Undated.
"Standard Terminology Relating to Plastics", American Society for Testing Materials, Designation: D883-00, pp. 1-15, Undated.
Hendricks et al., "Rubber-Related Polymers I. Thermoplastic Elastomers", Rubber Technology, pp. 515-533, Undated.
Office Action for U.S. Appl. No. 10/389,448 dated Feb. 25, 2009; P&G Case Z-3801; Braun et al.; filed Mar. 14, 2003.
Office Action for U.S. Appl. No. 10/389,448 dated Feb. 22, 2007; P&G Case Z-3801; Braun et al.; filed Mar. 14, 2003.
Office Action for U.S. Appl. No. 12/186,639 dated Dec. 23, 2009; P&G Case Z-3801CCC; Braun et al.; filed Aug. 6, 2008.
Office Action for U.S. Appl. No. 10/830,693 dated Feb. 26, 2009; P&G Case Z-3602; Masterman et al.; filed Apr. 23, 2004.
Office Action for U.S. Appl. No. 10/830,693 dated Jul. 2, 2008; P&G Case Z-3602; Masterman et al.; filed Apr. 23, 2004.
Office Action for U.S. Appl. No. 10/830,693 dated Mar. 3, 2008; P&G Case Z-3602; Masterman et al.; filed Apr. 23, 2004.
Office Action for U.S. Appl. No. 10/830,693 dated Oct. 24, 2007; P&G Case Z-3602; Masterman et al.; filed Apr. 23, 2004.
Office Action for U.S. Appl. No. 10/830,693 dated May 15, 2007; P&G Case Z-3602; Masterman et al.; filed Apr. 23, 2004.
Office Action for U.S. Appl. No. 10/830,693 dated Aug. 17, 2006; P&G Case Z-3602; Masterman et al.; filed Apr. 23, 2004.
Office Action for U.S. Appl. No. 10/799,793 dated Jun. 19, 2009; P&G Case Z-3801C; Braun et al.; filed May 2, 2007.
Office Action for U.S. Appl. No. 10/799,793 dated Apr. 25, 2008; P&G Case Z-3801C; Braun et al.; filed May 2, 2007.
Office Action for U.S. Appl. No. 10/820,562 dated Jun. 4, 2010; P&G Case Z-3710E; Braun et al.; filed Mar. 16, 2000.
Office Action for U.S. Appl. No. 10/820,562 dated Jul. 27, 2009; P&G Case Z-3710E; Braun et al.; filed Mar. 16, 2000.
Office Action for U.S. Appl. No. 10/820,562 dated Jul. 5, 2007; P&G Case Z-3710E; Braun et al.; filed Mar. 16, 2000.
Office Action for U.S. Appl. No. 10/820,562 dated May 8, 2006; P&G Case Z-3710E; Braun et al.; filed Mar. 16, 2000.
Office Action for U.S. Appl. No. 10/820,562 dated Aug. 15, 2008; P&G Case Z-3710E; Braun et al.; filed Mar. 16, 2000.
U.S. Appl. No. 12/546,066, filed Aug. 24, 2009, Masterman et al.

U.S. Appl. No. 12/186,639, filed Aug. 6, 2008, Braun et al.
U.S. Appl. No. 10/820,562. filed Mar. 16, 2000 Braun et al.
U.S. Appl. No. 12/828,653, filed Jul. 1, 2010 Braun et al.

U.S. Appl. No. 12/828,667, filed Jul. 1, 2010 Braun et al.

* cited by examiner

FIG. 8
FIG. 9
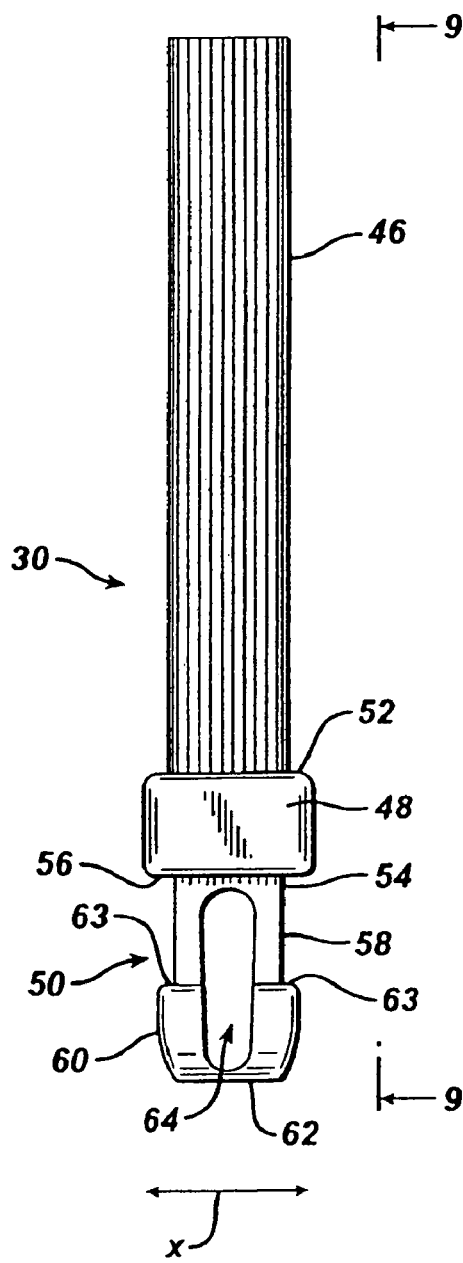
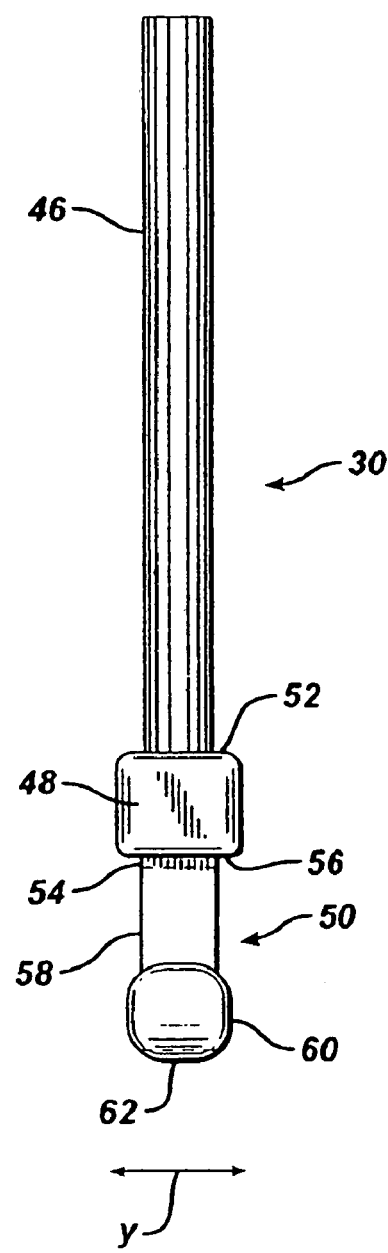

TOOTHBRUSH HEAD

CROSS-REFERENCE TO RELATED APPLICATIONS

This application is a continuation of U.S. application Ser. No. 11/799,733 filed May 2, 2007, now abandoned which is a continuation of U.S. application Ser. No. 10/389,448 filed Mar. 14, 2003, now abandoned both of which are incorporated herein by reference. Cross-reference is also made to U.S. patent application Ser. No. 09/526,679 filed on Mar. 16, 2000, now U.S. Pat. No. 6,553,604, and Ser. No. 09/576,590 filed on May 22, 2000, now U.S. Pat. No. 6,564,416, both of which are assigned to Gillette Canada Company.

FIELD OF THE INVENTION

The invention relates generally to the field of oral care, and in particular to toothbrushes. More specifically, the invention relates to a toothbrush head having one or more pivoting tufts of bristles, the head having two portions that can move independent of each other.

BACKGROUND OF THE INVENTION

A Japanese patent document having an application number of 3-312978 discloses a toothbrush having a multiplicity of tufts of nylon bristles. In a first embodiment shown in FIGS. 1, 2 and 3 of the document, a plurality of cylindrical recessed sections in the head are set orthogonally to the longitudinal axial direction of a shank and are formed at equal intervals. Column-shaped rotary bodies 5 are respectively contained in the recessed sections. On the peripheral surfaces of the rotary bodies 5, along the axial direction, projected strip sections 5a are formed, and they are set in a state that they are positioned at the opening sections of the recessed sections. At the opening sections of the recessed sections, contact surfaces to be positioned on both the sides are formed. At both the ends of the upper surfaces of the projected strip sections 5a, nylon bristles 6 are arranged to be vertically erected.

As shown in FIG. 3 of the document, the arrangement described above allows bristles 6 to rotate during use of the brush. A problem with this brush is that two tufts of bristles are secured to each strip section 5a and thus must rotate in unison. As a result, an individual tuft of bristles cannot rotate independently of its "partner" tuft. The individual tuft may thus be prevented from achieving optimal penetration between two teeth during brushing because the partner tuft might contact the teeth in a different manner and interfere with rotation of the individual tuft.

FIGS. 4, 5 and 6 of the document disclose a second embodiment in which each tuft of bristles is secured to the head by a ball and socket type arrangement. While this embodiment allows each tuft of bristles to swivel independent of the other tufts, it does have disadvantages. If a tuft of bristles is tilted out towards the side of the head and that tuft is positioned near the interface between the side and top surfaces of the teeth, chances are increased that the bristle tips will not even be in contact with the teeth during brushing. Further, the random orientation in which the tufts can end up after brushing detracts from the attractiveness of the brush.

The Japanese reference also discloses that the brush head is made of a unitary structure. As such, water cannot flow through any central portion of the brush head, thereby inhibiting the cleanability of the brush. Further, the unitary head structure does not allow different portions of the head to move independently of each other. Accordingly, the bristle tufts extending from the tuft cannot accommodate the varying tooth surfaces as well as a brush in which the head has two or more portions that can move or flex independent of each other.

SUMMARY OF THE INVENTION

The present invention is directed to overcoming one or more of the problems set forth above. Briefly summarized, according to one aspect of the present invention, a toothbrush head has a tooth cleaning element extending from the head. The head is divided into at least two portions which can be moved independent of each other. The tooth cleaning element is rotatable relative to that portion of the head from which it extends.

According to another aspect of the invention, a tooth cleaning element includes one or more tooth cleaners, a base support, and an anchor pivot. One end of the one or more tooth cleaners is secured to a first end of the base support. One end of the anchor pivot is secured to a second end of the base support. The anchor portion has a larger section further from the base support than a smaller section of the anchor portion.

In accordance with a third aspect of the invention, a method of making a toothbrush head includes molding a plastic toothbrush head in a mold. The head has two distinct portions which are spaced a predetermined distance from each other. The head is removed from the mold. At least that part of the head where the two head portions connect is heated. The two head portions are moved towards each other. At least that part of the head where the two head portions connect is cooled such that the two head portions will now remain in positions where they will be spaced apart a distance which is less than the predetermined distance.

According to a fourth aspect of the invention, a method of making a toothbrush head includes molding a plastic toothbrush head in a mold. The head has at least one hole therein which extends all the way through the head. The head is removed from the mold. A tooth cleaning element is inserted into the hole These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 8 is a front view of a pivoting tuft taken along the lines 8-8 of FIG. 13;

FIG. 9 is a side view of the pivoting tuft of FIG. 8 taken along lines 9-9;

DETAILED DESCRIPTION

Figure 5:
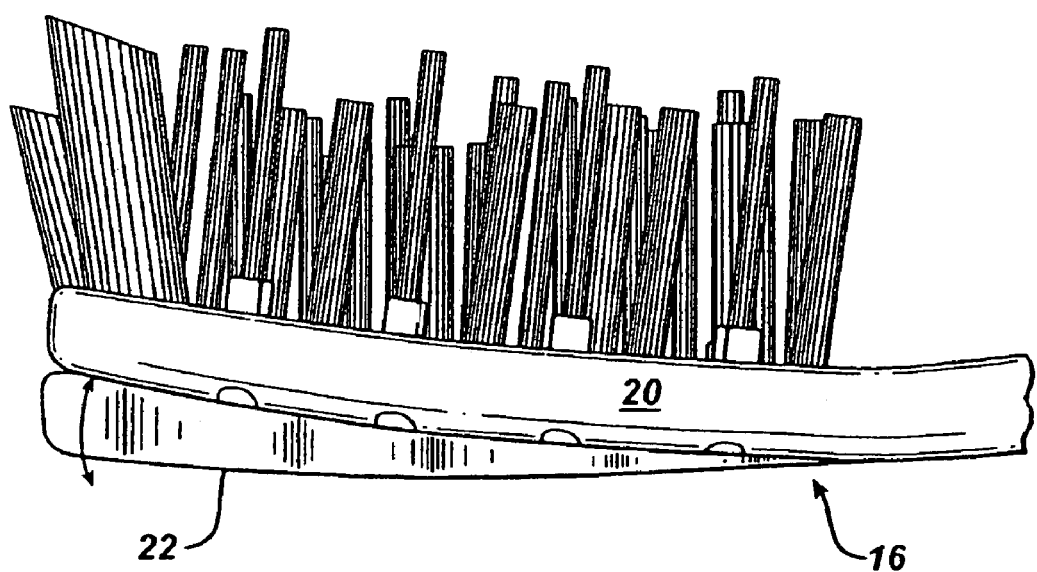
FIG. 5 is a side view of the head of FIG. 1 showing one of the head portions flexing.

Beginning with FIGS. 1-5, there is shown a toothbrush head 16 which extends from a neck 14 which extends from a handle (not shown) to form a toothbrush. The type of handle is not germane to the present invention. The head and handle are preferably made of polypropylene. The head has a serpentine split 18 which divides the head into two portions 20 and 22. An end of the split 13 near neck 14 is preferably circular in shape (see FIG. 2). As shown in FIG. 5, the split in the head allows portions 20 and 22 to flex or move independent of each other during use of the toothbrush, thus facilitating cleaning of the teeth.

Split 18 can also be defined as an opening in the head between head portions 20 and 22. This opening allows water to flow through the head, thereby enhancing cleaning of the top head surface which typically gets caked with toothpaste in spite of efforts to rinse the head clean.

Head portion 20 includes a projecting part 24 which fits (at least partially) into a recess 26 (see FIG. 6) defined by portion 22. Projecting part 24 has several tufts of bristles extending from it (to be described in further detail below) and is surrounded on three sides by head portion 22.

Figure 1:
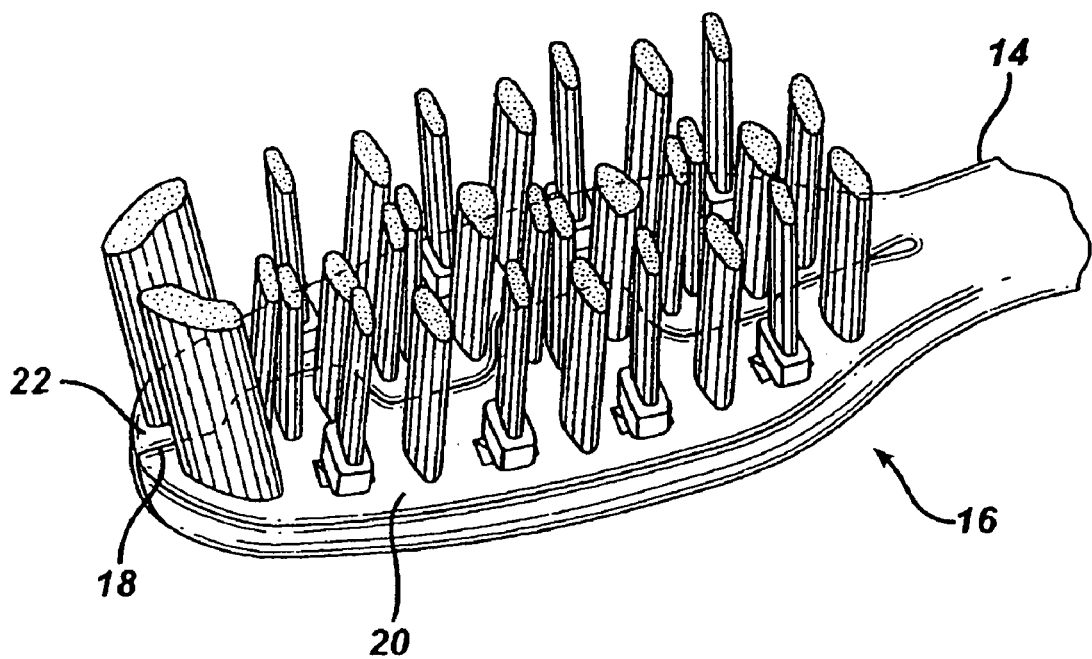
FIG. 1 is a perspective view of the toothbrush head of FIG. 1.
Figure 2:
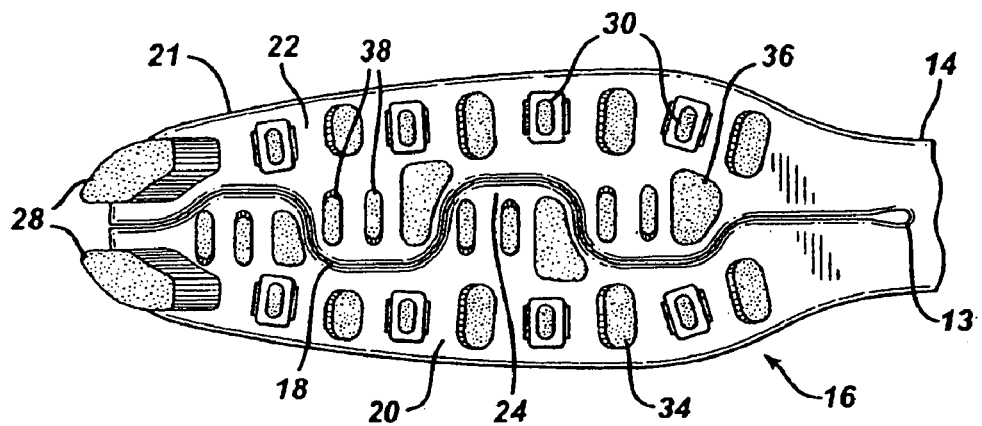
FIG. 2 is a top view of the head of FIG. 1.
Figure 3:
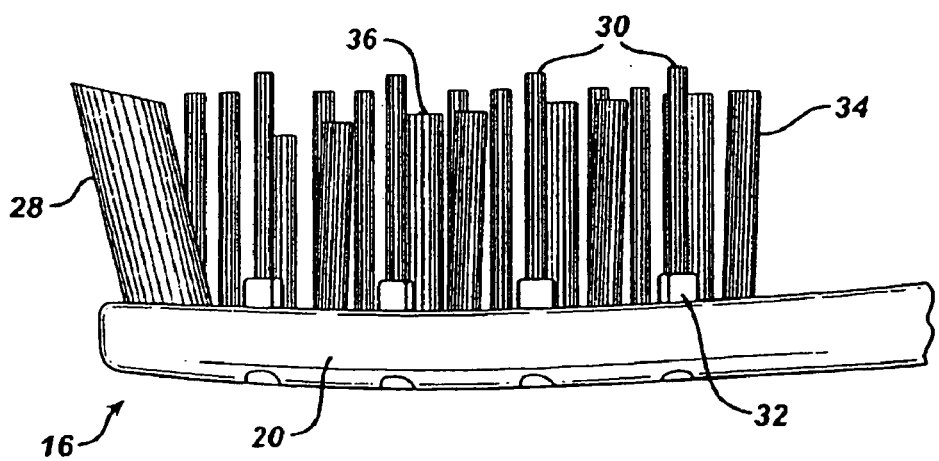
FIG. 3 is a side view of the head of FIG. 1.
Figure 4:
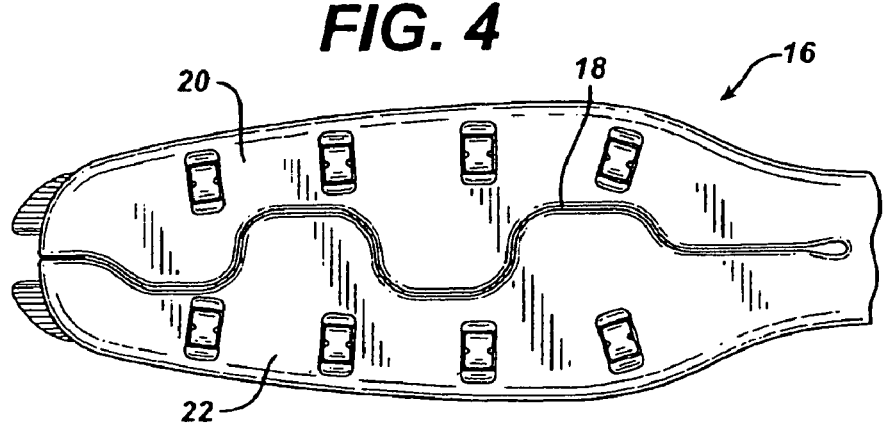
FIG. 4 is a bottom view of the head of FIG. 1.

Referring now to FIGS. 2 and 3, each of the tufts of bristles on head 16 will be described. A first pair of tufts 28 are located towards the free end of the head, one on each head portion 20, 22. Each tuft has bristles (tooth cleaners) which preferably are each made of polybutylene-terepthalate (PBT) and have a diameter of 0.007 inches. The shortest bristles in tuft 28 have a length of 0.420 inches with the remaining bristles increasing in length steadily to a tip of the tuft. Each tuft tilts away from the handle by an angle of preferably about 12 degrees relative to that portion of the surface of the head from which it projects. As shown in FIG. 2, tufts 28 have a larger cross-section than any other tuft on the head.

A second group of tufts are pivoting tufts 30 (the only tufts on the head which are rotatable). There are four tufts 30 on each head portion 20, 22 which are located towards the outside of the head. Each tuft 30 can pivot up to about 15 degrees to either side of a vertical position on the head, more preferably being able to pivot up to about 8 degrees to either side of a vertical position on the head. The pivoting of tufts 30 is roughly towards or away from neck 14. Each tuft 30 includes a base support 32 made of polypropylene. The bristles are made of polyamid 6.12, have a diameter of 0.008 inches and extend 0.420 inches above the base support.

A third group of tufts 34 extend perpendicular to the head. There are four tufts 34 on each head portion 20, 22 which alternate with tufts 30. When viewed from the top (FIG. 2) the tufts are oval in shape (similar to tufts 30 but larger). In other words, the tufts 34 and 30 have oval shaped cross-sections.

Each tuft 34 has bristles which are made of polyamid 6.12, have a diameter of 0.006 inches and extend above the head by about 0.385 inches.

A fourth group of tufts 36 are located towards the inside of the head. There are two such tufts on each head portion 20, 22. Each tuft 36 extends perpendicular to the head. The bristles of tuft 36 have a diameter of 0.006 inches, are made of polyamid 6.12 and rise about 0.360 inches above the head.

A fifth and final group of tufts 38 are also located towards the inside of the head (away from a perimeter 21 of the head). There are 4 pairs of tufts 38. In each pair one tuft is closer to neck 14 than the other tuft. In each pair of tufts 38, (a) a base of one tuft is closer to a first side of the head and this one tuft leans towards a second side of the head, and (b) a base of the other tuft is closer to the second side of the head and this other tuft leans towards the first side of the head. As such, the tufts in each pair lean across each other. The angle of tilt towards the side of the head is about five degrees. Each tuft 38 bristles which are made of PBT, have a bristle diameter of about 0.007 inches and extend about 0.460 inches above head 16. Each tuft 38 has an oval cross-section with a long dimension of the oval being oriented in the direction of tilt.

The bristles used on the head can be crimped (see U.S. Pat. No. 6,058,541) or notched (see U.S. Pat. No. 6,018,840). Other types of tooth cleaners besides bristles can be used. For example, a tuft of bristles could be replaced by an elastomeric fin. The US patents listed in this paragraph are incorporated herein by reference.

Figure 6:
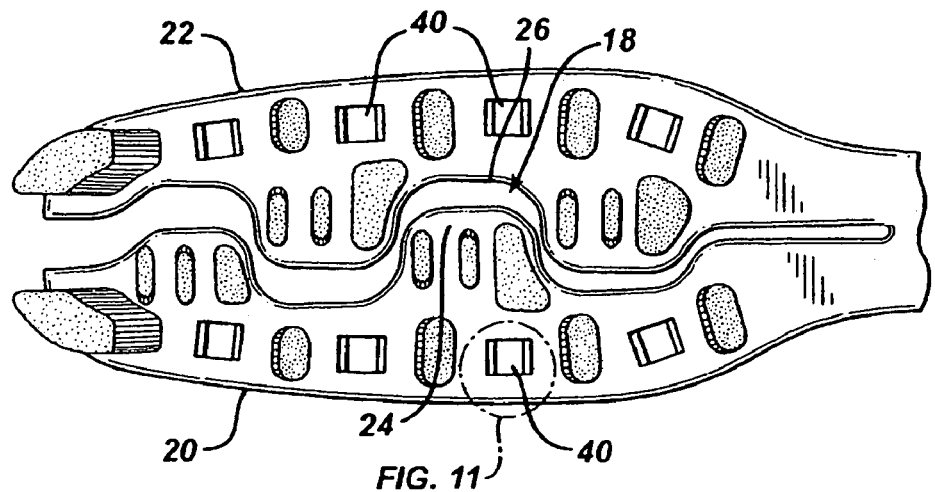
FIG. 6 is a top view of the head of FIG. 1 with the two head portions separated from each other.

Turning now to FIG. 6, a description will now be provided as to how the toothbrush (head) is made. In a first step, the head, neck and handle of the toothbrush are injection molded in a mold. During this injection molding step, tufts 28, 34, 36 and 38 are secured in the head by a hot-tufting process. Hot-tufting processes are notoriously well known by those skilled in the art (see e.g. U.S. Pat. Nos. 4,635,313; and 6,361,120; British patent application 2,330,791; and European patent application 676,268 A1).

Briefly, hot-tufting involves presenting ends of a multiplicity of groups of plastic filaments into a mold. Each group of filament ends inside the mold is optionally melted into a blob. Each filament group is cut to a desired length (either before or after being introduced into the mold) to form a tuft of bristles. The mold is closed and molten plastic is injected into the mold. When the plastic solidifies, it locks one end of the tufts of bristles into the head of the toothbrush.

It can be seen in FIG. 6 that the opening 18 between head portions 20 and 22 is much wider at this point than in the heads final form (see FIG. 2). In other words, head portions 20 and 22 are spaced a predetermined distance (preferably at least about 1 mm) from each other. Further, through holes 40 are created during the molding step for receiving pivoting tufts 30 at a later point in the manufacturing process. Holes 40 will be described in greater detail below.

Figure 7:
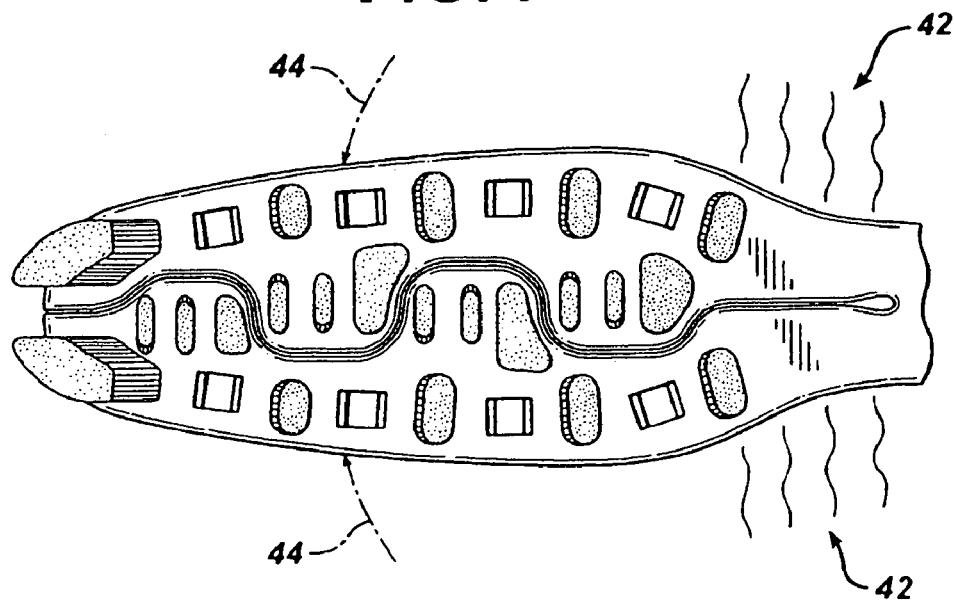
FIG. 7 is a top view of the head of FIG. 1 after the head portions have been positioned closer to each other.

With reference to FIG. 7, after the toothbrush is removed from the mold, heat 42 is applied to the head near the neck and to part of the neck (hereinafter the neck). The heat can be applied in a number of ways including hot air, radiant heating, ultrasonic or convection (e.g. hot oil) heating. Here the heat is shown being applied to the sides of the neck. It is preferable to apply the heat to the top and bottom surface of the neck. The heat brings the plastic up to 1.0-1.12 times its glass transition temperature (when temperatures are measured in the Kelvin scale). The plastic should not be heated above 1.12 times its glass transition temperature in order to avoid damaging the plastic. More preferably, the plastic is heated to about 1.03-1.06 times its glass transition temperature (measured in degrees Kelvin). The glass transition temperature for polypropylene is about 100 degrees centigrade whereas the glass transition temperature for copolyester and polyurethane is about 65 degrees centigrade.

Pressure 44 is then applied to head portions 20, 22 to move the portions towards each other. Once head portions 20, 22 are in the position shown in FIG. 2, the heated portion of the head/neck is cooled by, for example, exposing the heated portion to a cold gas or liquid. If room temperature air is used to cool the neck, such air should be applied for about 20-25 seconds. This has the effect of forming the two head portions into their final positions.

In order to achieve short process times, the highest temperature heat source which will not damage the plastic should be used. If too hot a heat source is used and/or if the heat is applied for too long, the plastic can be damaged. If the heat source is not hot enough, the process will take too long and/or head portions 20, 22 will not remain in their final desired positions. If the head/neck are made of polypropylene and hot air is used to heat the neck, (a) the heated air should be at a temperature of about 170 degrees centigrade and should be applied to the neck for about 70 seconds, (b) the polypropylene should be raised to a temperature of about 140 degrees centigrade, and (c) a nozzle which applies the hot air to the neck should be about 10 mm from the neck.

If copolyester or polyurethane is used as the material for the head neck, (a) the heated air should be at a temperature of 250 degrees centigrade and should be applied to the neck for about 10 seconds, (b) the material should be raised to a temperature of preferably 95-100 degrees centigrade, and (c) a nozzle which applies the hot air to the neck should be about 15-20 mm from the neck.

Heating the respective materials above for the time indicated allows the material to be softened and mechanically bent into its final form. Exceeding the heating times above could cause the material to overheat and become damaged.

Turning to FIGS. 8 and 9, each pivoting tuft 30 has a multiplicity of bristles 46, a base support 48 and an anchor pivot 50. The bristles are secured to and extend from a first end 52 of the base support while a first end 54 of the anchor pivot extends from a second end 56 of the base support. The base support and anchor pivot are preferably a unitary structure made of the same material. Anchor pivot 50 includes a first portion 58 near the first end 54 and a second portion 60 near a second end 62 of the anchor pivot. First portion 58 is smaller in an X an Y dimension than second portion 60. Base support 48 is larger in an X and Y dimension than second portion 60 of the anchor support. Second portion 60 includes a pair of lips 63. The anchor pivot defines an opening 64 therethrough.

Tuft 30 can also be made by a hot-tufting type process as described above. Instead of injecting plastic into the mold to form a toothbrush handle, neck and head, the plastic is injected into a mold to form base support 48 and anchor pivot 50, capturing bristles 46 when the injected plastic cools.

Figure 10:
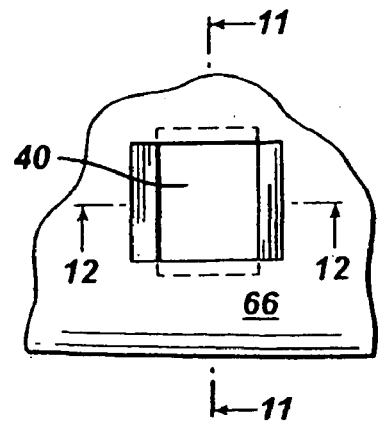
FIG. 10 is a top view of one of the holes in the head for receiving the pivoting tuft (see FIG. 6)
Figure 11:
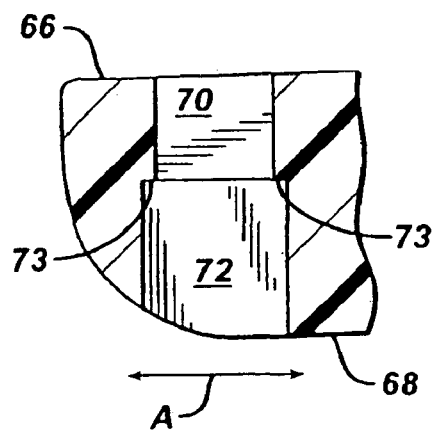
FIG. 11 is a sectional view of FIG. 10 taken along lines 11-11.
Figure 12:
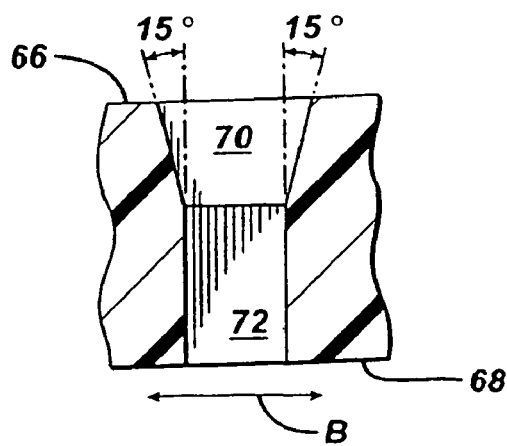
FIG. 12 is a sectional view of FIG. 10 taken along lines 12-12.

With reference to FIGS. 10-12, through holes 40 (FIG. 6) will now be described. Each hole 40 extends from a top surface 66 of the brush head through a bottom surface 68. Hole 40 includes first and second portions 70 and 72. Portion 72 is substantially a parallelepiped except that some of its lower section is rounded off (see FIG. 11). Portion 70 is also substantially a parallelepiped except that two of its sides are flared to the sides by about 15 degrees (see FIG. 12). Hole portion 72 is longer in a dimension A than hole portion 70 (FIG. 11). Hole portion 70 has about the same width in a dimension B as hole portion 72 where hole portions 70 and 72 meet (FIG. 12). Dimensions A and B are substantially perpendicular to each other in this embodiment. A pair of lips 73 are defined by this arrangement.

Figure 13:
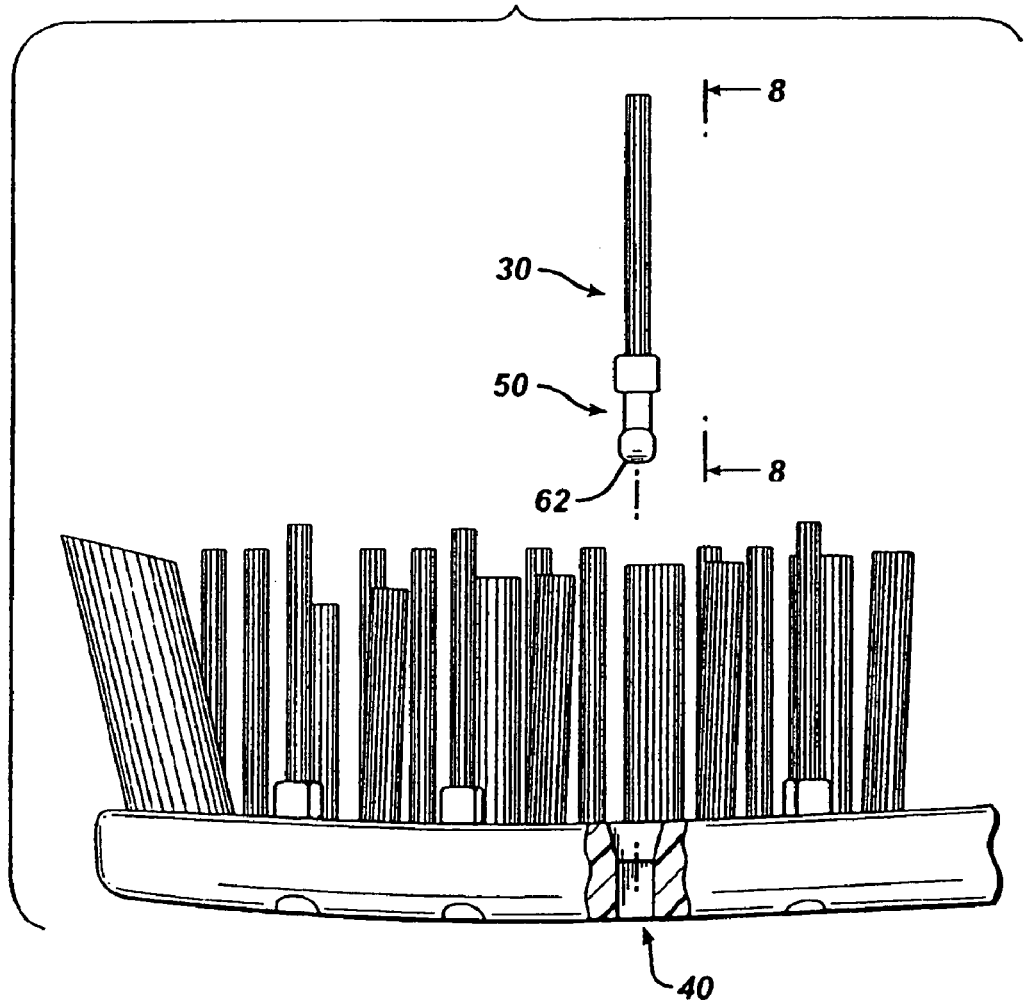
FIG. 13 is a side view of the head of FIG. 1 (a portion is removed to facilitate viewing) and a pivoting tuft prior to insertion into the head.
Figure 14:
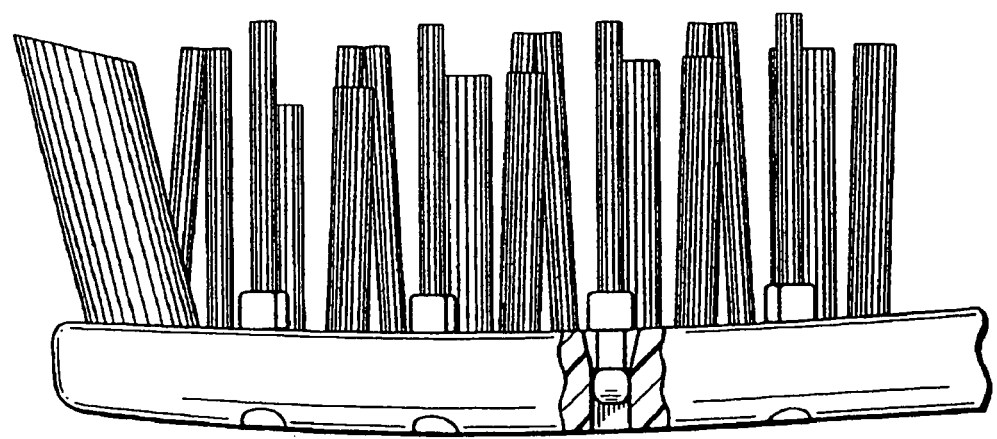
FIG. 14 is a side view of the head of FIG. 1 (a portion is removed to facilitate viewing) and a pivoting tuft after insertion into the head.

Turning now to FIGS. 13-16, the insertion of pivoting tufts 30 into holes 40 will be described. A tuft 30 is positioned over a hole 40 with end 62 of anchor pivot 50 facing the hole (FIG. 13). As shown in FIGS. 16A-C, tuft 30 is moved towards hole 40 until end 62 starts to enter the hole (FIG. 16A). Tuft 30 is then pressed into the hole causing sides of hole portion 70 to squeeze second portion 60 of the anchor pivot. Accordingly, anchor pivot 50 collapses causing opening 64 to become temporarily smaller. Tuft 30 is then pushed all the way into hole 40 (FIG. 16C) at which point the resilient plastic anchor pivot springs back to its form shown in FIG. 16A. This paragraph describes a snap-fit retention of tuft 30 to the head.

Figure 16A:
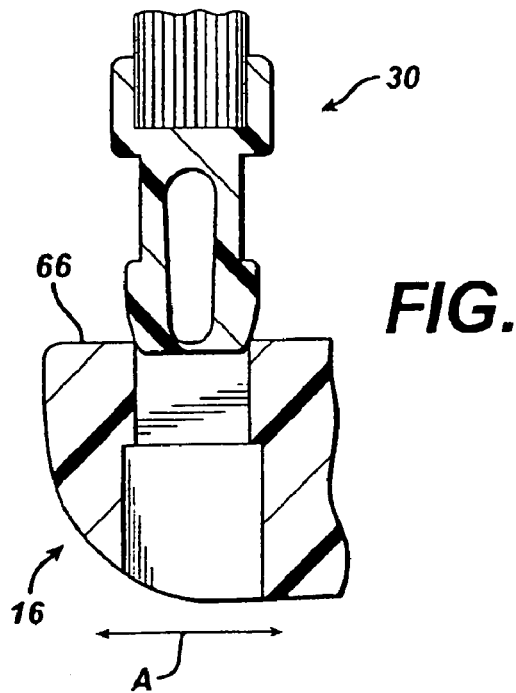
FIGS. 16A-C are sectional views of FIG. 15 taken along the lines 16A-C-16A-C.
Figure 16B:
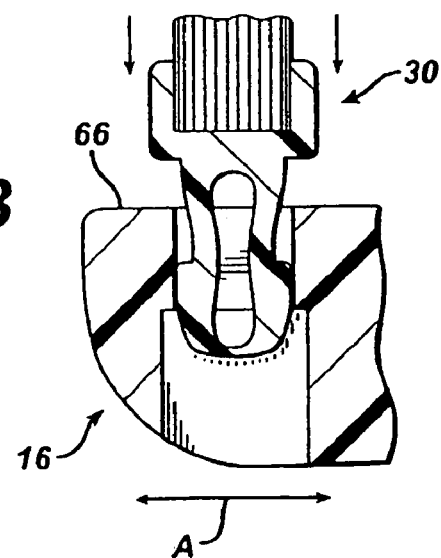
Figure 16C:
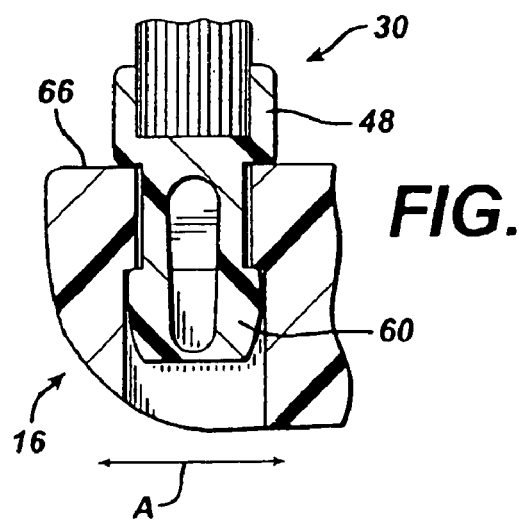

Referring to FIG. 16C, base support 48 is longer in the A dimension than hole portion 70 and thus prevents tuft 30 from being pressed further into hole 40. Second portion 60 is also longer in the A dimension than hole portion 70 and so prevents tuft 30 from moving back out of hole 40. This is due to the fact that lips 63 (FIG. 8) engage lips 73 (FIG. 11). This arrangement also prevents tuft 30 from rotating about the long axis of the bristles.

Figure 15:
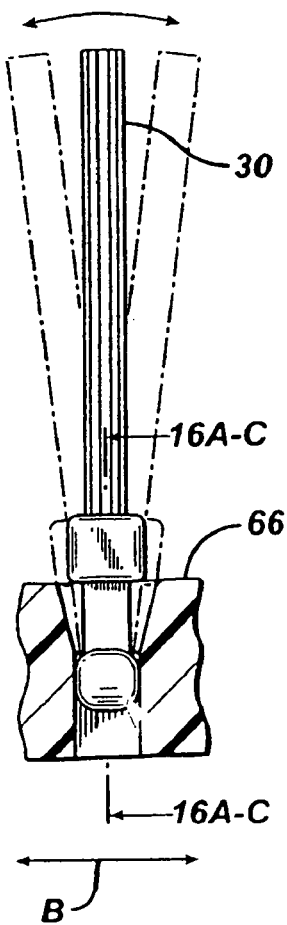
FIG. 15 is a side view of the pivoting tuft showing its motion.

As shown in FIG. 15, tuft 30 pivots when it is engaged by, for example, portions of the oral cavity during brushing. Preferably each tuft 30 can pivot up to about 15 degrees to either side of a position perpendicular to surface 66.

Figure 17:
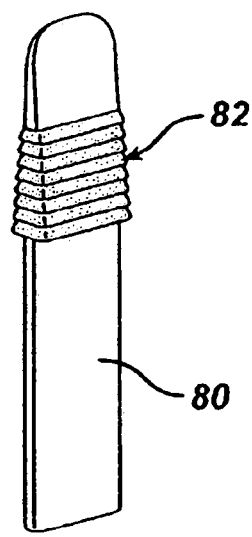
FIG. 17 is a perspective view of a tooth cleaner in the form of a ribbed fin.
Figure 18:
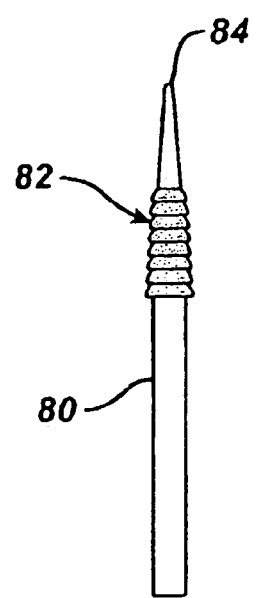
FIG. 18 is a side view of the ribbed fin of FIG. 17.

Turning to FIGS. 17 and 18, another type of tooth cleaning element in the form of a fin 80 is disclosed. Each fin is supported by a base support 48 and an anchor pivot 50 (both not shown) as described above, allowing the fin to pivot on the brush head. Alternatively, a fin can be securely affixed to the head so that it does not pivot. The fin is created of a thermoplastic elastomer (TPE) by an injection molding process. In this embodiment, a textured surface is provided by a series of ribs 82. These ribs enhance cleaning of the oral cavity. The ribs are formed by injection molding a TPE over the fin. The ribs are preferably softer than the fin. Alternative textured surfaces (e.g. dimples) can be used in place of the ribs.

As shown in FIG. 18, the fin has a width of preferably about 0.030 inches. The long dimension of the fin above the base support is preferably 0.420 inches. A tip 84 of fin 80 has a width of preferably 0.007 inches. The distance from the base of the ribs to tip 84 is about 0.168 inches whereas the distance from the top of the ribs to the tip is about 0.079 inches. The top of the ribs have a width of about 0.035 inches. The ribs (textured surface) preferably extend about 2-12 mil away from said fin.

The invention has been described with reference to a preferred embodiment. However, it will be appreciated that variations and modifications can be effected by a person of ordinary skill in the art without departing from the scope of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush head having a longitudinal axis and a lateral axis, the lateral axis being perpendicular to the longitudinal axis, the lateral axis being generally parallel to a top surface, the toothbrush head further comprising:
the top surface, a bottom surface, and a hole having an entrance in the top surface of the head and extending from the top surface to the bottom surface, wherein the hole has a length parallel to the lateral axis and a width parallel to the longitudinal axis, wherein the hole has an upper section disposed adjacent the top surface and a lower section extending to the bottom surface;
one or more tooth cleaning elements extending from the top surface, each of the one or more tooth cleaning elements comprising a tooth cleaning portion, a base support, and an anchor pivot, wherein one end of the tooth cleaning portion is secured to a first end of the base support and a first end of the anchor pivot extends from a second end of the base support, wherein the anchor pivot is pivotably disposed within the hole, wherein the anchor pivot has a first portion near the first end of the anchor pivot and a second portion near the second end of the anchor pivot, wherein the first portion is smaller than the second portion, wherein the first portion and the second portion each have a length parallel to the lateral axis and a width parallel to the longitudinal axis, wherein each of the lengths of the first portion and the second portion are greater than their respective widths, wherein the second portion of the anchor pivot resides in the lower section of the hole, and wherein the lower section has about the same length and width as the length and width of the second portion of the anchor pivot.

2. The toothbrush head of claim 1, wherein the upper section of the hole has a length which is shorter than the length of the lower section of the hole.

3. The toothbrush head of claim 2, wherein the lower section of the hole has a width which is about the same as the width of the upper section of the hole where the hole sections meet, the width of the upper section of the hole flaring from where the hole sections meet towards the top surface.

4. The toothbrush head of claim 3, wherein sides of the upper section of the hole flare by about 15 degrees.

5. The toothbrush head of claim 1, wherein the anchor pivot comprises an opening extending therethrough.

6. The toothbrush head of claim 5, wherein the opening extends through the width of the anchor pivot.

7. The toothbrush head of claim 1 further comprising a first plurality of tooth cleaning elements extending from a free end of the toothbrush head.

8. The toothbrush head of claim 7 wherein each of the first plurality of tooth cleaning elements extends from the toothbrush head at an angle.

9. The toothbrush head of claim 1, wherein the one or more tooth cleaning elements are capable of pivoting with respect to the toothbrush head.

10. The toothbrush head of claim 9 further comprising a second plurality of cleaning elements extending from the toothbrush head adjacent a perimeter of the toothbrush head.

11. The toothbrush head of claim 10 further comprising a second plurality of cleaning elements and the one or more tooth cleaning elements are spaced alternatingly along the perimeter of the head with the one or more tooth cleaning elements.

12. The toothbrush head of claim 1, wherein the one or more tooth cleaning elements comprise a fin.

13. The toothbrush head of claim 12, wherein the fin comprises a thermoplastic elastomer.

14. The toothbrush head of claim 12, wherein the fin comprises a textured surface.

15. The toothbrush head of claim 14, wherein the textured surface comprises a plurality of ribs.

16. The toothbrush head of claim 14, wherein the textured surface is softer than the fin.

17. The toothbrush head of claim 14, wherein the textured surface is spaced from a tip of the fin.

18. The toothbrush head of claim 1, wherein the one or more tooth cleaning elements comprise a bristle tuft, and wherein are crimped or notched.

19. The toothbrush head of claim 1, wherein the one or more tooth cleaning elements comprise an elastomeric fin, and wherein the elastomeric fin comprises a surface texture.

20. The toothbrush head of claim 1, further comprising a split which separates the head into portions which can move relative to one another.

21. A toothbrush head having a longitudinal axis and a lateral axis, the lateral axis being perpendicular to the longitudinal axis, the lateral axis being generally parallel to a top surface, the toothbrush head further comprising:
the top surface, a bottom surface, and a hole having an entrance in the top surface of the head and extending from the top surface to the bottom surface, wherein the hole has a length parallel to the lateral axis and a width parallel to the longitudinal axis, wherein the hole has an upper section disposed adjacent the top surface and a lower section disposed near the bottom surface, and wherein the upper section of the hole has a length which is shorter than the length of the lower section of the hole;
one or more tooth cleaning elements extending from the top surface, each of the one or more tooth cleaning elements comprising a tooth cleaning portion, a base support, and an anchor pivot, wherein one end of the tooth cleaning portion is secured to a first end of the base support and a first end of the anchor pivot extends from a second end of the base support, wherein the anchor pivot is pivotably disposed within the hole, wherein the anchor pivot has a first portion near the first end of the anchor pivot and a second portion near the second end of the anchor pivot, wherein the first portion is smaller than the second portion, wherein the first portion and the second portion each have a length parallel to the lateral axis and a width parallel to the longitudinal axis, wherein each of the lengths of the first portion and the second portion are greater than their respective widths, wherein the second portion of the anchor pivot resides in the lower section of the hole, and wherein the lower section has about the same length and width as the length and width of the second portion of the anchor pivot.

22. The toothbrush head of claim 21, wherein the lower section of the hole has a width which is about the same as the width of the upper section of the hole where the hole sections meet, the width of the upper section of the hole flaring from where the hole sections meet towards the top surface.

23. The toothbrush head of claim 22, wherein sides of the upper section of the hole flare by about 15 degrees.

24. A toothbrush head comprising:
an opening having an entrance in a top surface of the head, wherein the opening has an upper portion disposed adjacent the top surface and a lower portion spaced from the top surface, and wherein the upper portion of the opening has a length which is shorter than the length of the lower portion of the opening, wherein the upper portion has a first width at the entrance in the top surface and a second width where the upper portion and the lower portion meet, and wherein the first width is greater than the second width; and an elastomeric tooth cleaning element having a base portion and a cleaning portion, the cleaning portion extending from the top surface of the head, the elastomeric tooth cleaning element being fixed to the head such that the tooth cleaning element does not rotate, and wherein the base portion is formed of a resilient material.

25. The toothbrush head of claim 24, wherein the base portion comprises a first section and a second section, wherein the second section resides in the lower section of the opening, and wherein the second section has a length which is greater than that of the first section.

26. The toothbrush head of claim 24, wherein a shoulder transitions between the length of upper portion and the length of the lower portion.

27. The toothbrush head of claim 24, further comprising a second plurality of bristle tufts having a second height, wherein the elastomeric tooth cleaning elements have an elastomeric tooth cleaning element height, and wherein the second height is less than the elastomeric tooth cleaning element height.

28. The toothbrush head of claim 27, wherein the first plurality of bristle tufts are disposed on a free end of the head and increasing in height to a tip at the free end.

* * * * *